United States Patent [19]

Mikite et al.

[11] 4,127,576
[45] Nov. 28, 1978

[54] NORTROPINE-CARBAZATE DERIVATIVES

[75] Inventors: Gyula Mikite; Lujza Petocz; Ibolya Kosoczky; Katalin Grasser, all of Budapest, Hungary

[73] Assignee: Egyt Gyogyszervegyeszeti Gyar, Budapest, Hungary

[21] Appl. No.: 855,705

[22] Filed: Nov. 29, 1977

[30] Foreign Application Priority Data

Dec. 8, 1976 [HU] Hungary .............................. EE 2463

[51] Int. Cl.$^2$ ..................... C07D 471/08; A61K 31/46
[52] U.S. Cl. .................................... 424/265; 546/125; 546/130; 260/244.4
[58] Field of Search ......................... 260/292; 424/265

[56] References Cited

U.S. PATENT DOCUMENTS 4,042,700   8/1977   Banholzer et al. ................... 260/292

OTHER PUBLICATIONS

Burger Medicinal Chemistry, Second Edit., Interscience, pub. p. 497 (1960).

Primary Examiner—Alan L. Rotman
Attorney, Agent, or Firm—Young & Thompson

[57] ABSTRACT

The invention relates to novel nortropine-carbazate derivatives of the general formula (I),

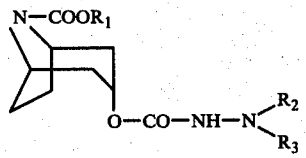

wherein
$R_1$ is $C_{1-4}$ alkyl, phenyl or halophenyl group,
$R_2$ is hydrogen or a $C_{1-4}$ alkyl, hydroxy-$C_{1-4}$ alkyl, $C_{1-4}$ acyl, phenoxycarbonyl or $C_{1-4}$ alkoxycarbonyl group, and
$R_3$ is hydrogen of a $C_{1-4}$ alkyl or $C_{1-4}$ acyl group, or $R_2$ and $R_3$ may form together a $C_{1-10}$ alkylene group attached
to the nitrogen atom with a double bond, as well as to pharmaceutically acceptable acid addition salts of said compounds.

The above compounds are new and can be applied as narcosis potentiating agents.

The compounds of the general formula (I) can be prepared by reacting a compound of the general formula (II),

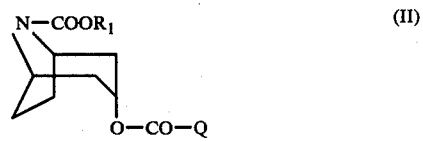

wherein $R_1$ is as defined above and Q is halogen, $C_{1-4}$ alkoxy or phenoxy, with a hydrazine compound of the general formula (III),

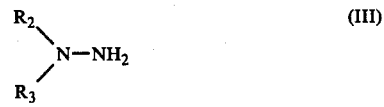

wherein $R_2$ and $R_3$ are as defined above. According to another method a compound of the general formula (II), wherein $R_1$ and Q are as defined above, is reacted with hydrazine or hydrazine hydrate, and the resulting compound of the general formula (I), wherein $R_2$ and $R_3$ are hydrogens and $R_1$ is as defined above, is converted into the corresponding N-substituted derivatives by methods known in the art.

14 Claims, No Drawings

NORTROPINE-CARBAZATE DERIVATIVES

The invention relates to novel nortropine-carbazate derivatives. More particularly, the invention relates to novel compounds having the general formula (I),

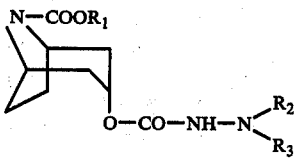  (I)

wherein
- $R_1$ is a $C_{1-4}$ alkyl, phenyl or halophenyl group,
- $R_2$ is hydrogen or a $C_{1-4}$ alkyl, hydroxy-$C_{1-4}$ alkyl, $C_{1-4}$ acyl, phenoxycarbonyl or $C_{1-4}$ alkoxycarbonyl group, and
- $R_3$ is hydrogen or a $C_{1-4}$ alkyl or $C_{1-4}$ acyl group, or $R_2$ and $R_3$ may form together a $C_{1-10}$ alkylene group attached to the nitrogen atom with a double bond.

The invention also relates to salts of the above compounds formed with organic or mineral acids. Of the acid addition salts those formed with pharmaceutically acceptable acids are the most preferred.

Of the new compounds according to the invention the following are to be mentioned:
- 8-ethoxycarbonyl-3α-hydrazinocarbonyloxy-nortropane hydrochloride,
- 8-phenoxycarbonyl-3α-hydrazinocarbonyloxy-nortropane,
- 8-phenoxycarbonyl-3α-hydrazinocarbonyloxy-nortropane hydrochloride,
- 8-phenoxycarbonyl-3α-hydrazinocarbonyloxy-nortropane hydrobromide,
- 8-phenoxycarbonyl-3α-hydrazinocarbonyloxy-nortropane sulfate,
- 8-phenoxycarbonyl-3α-hydrazinocarbonyloxy-nortropane phosphate,
- 8-phenoxycarbonyl-3α-hydrazinocarbonyloxy-nortropane p-toluene-sulfonate,
- 8-phenoxycarbonyl-3α-(2'-methyl-hydrazinocarbonyloxy)-nortropane,
- 8-phenoxycarbonyl-3α-(2'-/2''-hydroxyethyl/-hydrazinocarbonyloxy)-nortropane,
- 8-phenoxycarbonyl-3α-(ethylidene-hydrazinocarbonyloxy)-nortropane,
- 8-phenoxycarbonyl-3α-(2',2'-diacetyl-hydrazinocarbonyloxy)-nortropane, and
- 8-phenoxycarbonyl-3β-(hydrazinocarbonyloxy)-nortropane.

The novel compounds according to the invention possess narcosis potentiating effects. In this respect the following compounds are the most preferred:
- 8-ethoxycarbonyl-3α-hydrazinocarbonyloxy-nortropane hydrochloride,
- 8-phenoxycarbonyl-3α-hydrazinocarbonyloxy-nortropane, and
- 8-phenoxycarbonyl-3α-(2',2'diacetyl-hydrazinocarbonyloxy)-nortropane.

The invention also relates to pharmaceutical compositions containing an effective amount of a compound having the general formula (I) or an acid addition salt thereof.

The 8-phenoxycarbonyl and 8-alkoxycarbonyl derivatives of nortropinone are substances known in the art (J. Chem. Soc. 2017/1967/; Hungarian patent specification No. 161,067). Some of these known compounds are active against Parkinson's disease.

It has been found that the 3-hydrazinocarbonyloxy and 3-(substituted hydrazinocarbonyloxy) derivatives of 8-hydrocarbyloxycarbonyl-nortropinone possess particularly advantageous biological effects.

The substituent in position 3 may be attached to the molecule in α or β configuration. The invention encompasses both types of isomers as well as mixtures thereof.

The nortropinone-carbazate derivatives of the general formula (I) are prepared according to the invention by reacting a compound of the general formula (II),

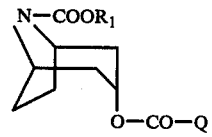  (II)

wherein $R_1$ is as defined above and Q stands for halogen, a $C_{1-4}$ alkoxy group or a phenoxy group, with a hydrazine compound of the general formula (III),

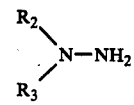  (III)

wherein $R_2$ and $R_3$ are as defined above.

The reaction is performed in an organic solvent which does not react with either of the reactants. When a compound of the general formula (II) containing a $C_{1-4}$ alkoxy or phenoxy group as substituent Q is applied as starting substance, the reaction is performed preferably in an aliphatic alcohol, such as methanol, ethanol, isopropanol or n-butanol.

When an acid halide of the general formula (II) (Q:halogen) is applied as starting substance, the reaction is performed preferably in an aromatic hydrocarbon, such as benzene or toluene, or in a chlorinated hydrocarbon, such as chloroform, dichloromethane or chlorobenzene. Mixtures of the above solvents, such as mixtures of benzene and chloroform, benzene and ethanol or chloroform and n-butanol, can also be applied as reaction media.

The reaction is performed preferably at a temperature between 0° C and 100° C. In some instances the reaction proceeds well at ambient temperature.

The starting compounds of the general formula (II) can be prepared from tropinone or tropine. When tropine is used in the reaction, a compound of α configuration is obtained, whereas pseudotropine leads to the formation of the β isomers.

When torpinone is applied as starting substance in the above reaction, this compound is reacted first with an appropriate chlorformate to form the required 8-alkoxycarbonyl or 8-aryloxycarbonyl-nortropinone, and this latter substance is reduced, preferably by catalytic hydrogenation, to obtain a nortropine derivative of the general formula (IV),

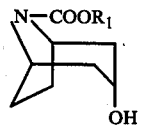  (IV)

wherein $R_1$ is as defined above. A compound of the general formula (II), wherein Q is chlorine and $R_1$ is as defined above, can be obtained by reacting a compound of the general formula (IV) with phosgene. The reaction is performed preferably in the presence of an acid binding agent. As acid binding agent preferably an organic base, such as pyridine, triethylamine, picoline, etc. is applied. The chlorine substituent of the resulting compound having the general formula (II) can be replaced by other halogens, such as bromine, according to methods known in the art.

If a compound of the general formula (IV) is reacted with a chloroformate of the general formula Cl—COOR$_7$, wherein $R_7$ represents a $C_{1-4}$ alkyl or phenyl group, a compound of the general formula (II) is obtained, wherein Q is $C_{1-4}$ alkoxy or phenoxy and $R_1$ is as defined above. These latter compounds can also be prepared by reacting tropine with a chloroformate of the general formula Cl—COOR$_1$, wherein $R_1$ is as defined above. In this instance tropine is reacted with two molar equivalents of the chloroformate.

According to another method of the invention the compounds of the general formula (I) are prepared by reacting a compound of the general formula (II) with hydrazine or hydrazine hydrate. In this instance compounds of the general formula (I), wherein $R_2$ and $R_3$ each represent hydrogen, are formed, which can be converted into N-monosubstituted or N,N-disubstituted carbazate derivatives by subsequent reactions.

Thus e.g. when a compound of the general formula (I), wherein $R_2$ is $C_{1-4}$ alkyl and $R_3$ is hydrogen or $R_2$ and $R_3$ represent the same $C_{1-4}$ alkyl group and $R_1$ is as defined above, is to be prepared, a compound of the general formula (I), wherein $R_2$ and $R_3$ represent hydrogen and $R_1$ is as defined above, is alkylated with an alkyl halide of the general formula $R_4$—Hal, wherein $R_4$ is a $C_{1-4}$ alkyl group and Hal stands for halogen. This reaction is performed in an inert organic solvent medium, preferably in the presence of an organic or mineral base.

When a compound of the general formula (I), wherein $R_3$ is hydrogen, $R_2$ is $C_{1-4}$ alkyl and $R_1$ is as defined above, is to be prepared, a compound of the general formula (I), wherein $R_2$ and $R_3$ represent hydrogen and $R_1$ is as defined above, is condensed with a $C_{1-4}$ aldehyde or ketone, and the condensation product is reduced in parallel with or after the condensation step.

In this instance the condensation step is performed preferably under reductive conditions. Reduction is performed preferably by catalytic hydrogenation.

When a compound of the general formula (I), wherein $R_1$ is as defined above and $R_2$ and $R_3$ form together a $C_{1-10}$ alkylene group attached to the nitrogen atom with a double bond, is to be prepared, a compound of the general formula (I), wherein $R_1$ is as defined above and $R_2$ and $R_3$ represent hydrogen, is condensed with a $C_{1-10}$ aliphatic aldehyde or ketone.

When a compound of the general formula (I), wherein $R_1$ is as defined above, $R_2$ is a $C_{1-4}$ acyl group and $R_3$ is hydrogen or a $C_{1-4}$ acyl group, is to be prepared, a compound of the general formula (I), wherein $R_1$ is as defined above and $R_2$ and $R_3$ represent hydrogen, is acylated with an acyl derivative of the general formula $R_5$COHal or $(R_5CO)_2O$, wherein $R_5$ is a $C_{1-4}$ alkyl group and Hal is halogen. If a monoacyl derivative is to be prepared, the acylating agent is applied in an amount equivalent with the 3-hydrazino-carbonyloxy-nortropane derivative and the reaction is performed in the presence of an acid binding agent, whereas if a diacyl compound is to be prepared, a large excess of the acylating agent is used.

Acylation is performed preferably in the presence of an inert organic solvent. As acid binding agent organic or mineral bases can be applied.

Those compounds of the general formula (I), wherein $R_2$ is a $C_{1-4}$ alkoxycarbonyl or phenoxycarbonyl group, $R_3$ is hydrogen and $R_1$ is as defined above, can be prepared by reacting a compound of the general formula (I), wherein $R_1$ is as defined above and $R_2$ and $R_3$ represent hydrogen, with a chloroformate of the general formula Cl-COOR$_6$, wherein $R_6$ represents a $C_{1-4}$ alkyl or phenyl group.

If desired, the compounds of the general formula (I) can be converted into their acid addition salts by reacting them with a pharmaceutically acceptble organic or mineral acid. The salt-formation is performed in a manner known per se.

The toxicities and narcosis potentiating effects of the novel compounds having the general formula (I) were studied on rats weighing 120 to 150 g. In the toxicity tests the animals were kept under observation for 7 days. The narcosis potentiating effect was studied on animals treated with an intravenous dosage of 50 mg/kg of hexabarbital (5-/1-cyclohexenyl/-1',5-dimethylbarbituric acid), and the prolongation of sleeping period was recorded. A 150% prolongated of sleeping period in relation to the controls was regarded as positive response. The number of animals with positive responses was related to the total number of animals treated. The results observed are summarized in Table 1. As reference substances chloropromazine (2-chloro-10-/3-dimethylaminopropyl/-phenothiazine), haloperidol [4-(4-chlorophenyl/-4-hydroxy-piperidyl)-4'-fluoro-butyrophenone] and diazepam (7-chloro-1-methyl-5-phenyl-1,2-dihydro-3-H-1,4-benzodiazepine-4-one) were applied.

Table 1

| Compound (Example No.) | LD$_{50}$ mg/kg p.o. | ED$_{50}$ mg/kg p.o. |
|---|---|---|
| 1 | 2000* | 0.54 |
| 3 | 5000 | 3.00 |
| 14 | 1200* | 1.00 |
| Chloropromazine | 210 | 4.7 |
| Haloperidol | 450 | 2.8 |
| Diazepam | 710 | 5.0 |

*The values are below the LD$_{50}$ values. No perishment was observed in the dosages indicated.

The data of Table 1 clearly demonstrate that the new compounds according to the invention are practically non-toxic (thus e.g. for the first compound even a dosage causing perishment could not be reached) and are effective in very small dosages.

The compounds of the invention do not influence the motility.

The effect of 8-phenoxycarbonyl-3-hydrazinocarbonyl-oxy-nortropane exerted on the motilities of mice was tested according to the method of Borsy et al. (Arch. Int. Pharmacodyn. 124, 1-2/1960/). The compound was administered orally in dosages of 20 to 80 mg/kg. The compound did not influence the motilities of the animals in the dosage range tested.

The above test method was applied also to study how 8-phenoxycarbonyl-3-hydrazinocarbonyloxy-nortropane does influence the hypermotility provoked with amphetamine (2-amino-1-phenyl-propane). Amphetamine was administered subcutaneously to mice in dosages of 7.5 mg/kg. The results are summarized in Table 2.

Table 2

| Compound (Example No.) | Dosage | Method of administration | Light interruption (average) |
|---|---|---|---|
| 5% carboxymethyl-cellulose solution | 20 ml/kg | p.o. | 318 |
| Amphetamine + + 5% carboxymethyl-cellulose solution | 7.5 mg/kg | s.c. | 583 |
| Amphetamine + + Ex. 3 | 7.5 mg/kg 40 mg/kg | s.c. p.o. | 270 |
| Amphetamine + + Ex. 3 | 7.5 mg/kg 80 mg/kg | s.c. p.o. | 175 |

The data of Table 2 demonstrate that 8-phenoxy-carbonyl-3-hydrazinocarbonyloxy-nortropane completely inhibited the development of the locomotor stimulating effect of amphetamine in both dosages examined.

The effect of 8-phenoxycarbonyl-3-hydrazinocarbonyloxy-nortropane exerted on the hypermotility provoked with amphetamine on rats was examined by the method of Janssen (Psychopharmacologia 1, 389-392/1960/). The stimulation of central nervous system was provoked with subcutaneous dosages of 7.5 mg/kg of amphetamine. The tests were performed on groups each consisting of 10 rats. The results are summarized in Table 3.

Table 3

| Compound (Example No.) | Dosage | Average values characterizing the behaviour of rats | | |
|---|---|---|---|---|
| | | Triangle walked in | Rearing | Washing |
| 0.9% saline solution | 20 ml/kg p.o. | 18.3 | 18.5 | 7.6 |
| 0.9% saline solution + + Ex. 3 | 20 ml/kg s.c. 40 mg/kg p.o. | 16.1 | 11.8 | 3.3 |
| 0.9% saline solution + + Amphetamine | 20 ml/kg p.o. 7.5 mg/kg s.c. | 28.5 | 28.6 | 2.7 |
| Ex.3 + + Amphetamine | 40 mg/kg p.o. 7.5 mg/kg s.c. | 14.5 | 21.5 | 0.6 |

The data of Table 3 demonstrate that the compound tested inhibits the appearance of hypermotility even in a dosage of 40 mg/kg.

The data of the pharmacological tests show that the new compounds according to the invention potentiate considerably the effects of narcotics on rats already in small dosages. The compounds have essentially no influence on the spontaneous motility of rats, they inhibit, however, the stimulating effect of amphetamine.

The new compounds according to the invention can be converted into pharmaceutical compositions by admixing them with adjuvants and/or auxiliary agents commonly used in the pharmaceutical industry. The pharmaceutical compositions to be administered orally, subcutaneously or intravenously (such as tablets, coated tablets, capsules, injections, etc.) contain generally 1 to 1000 mg of active agent in a dosage unit. These compositions can be applied in the therapy primarily for potentiating the effects of narcotics.

Combined pharmaceutical compositions, containing a narcotic along with a new compound according to the invention, can also be prepared. These compositions contain the new compounds in amounts sufficient to potentiate the effect of the narcotic concerned. The scope of the invention also extends to such compositions.

The invention is elucidated in detail by the aid of the following non-limiting Examples.

EXAMPLE 1

8-Ethoxycarbonyl-3α-hydrazinocarbonyloxy-nortropane hydrochloride 5.0 g (0.027 moles) of 8-ethoxycarbonyl-nortropine (prepared e.g. by the methd disclosed in Tetrahedron Letters 1971/1/57) are dissolved in 10 ml of toluene, and the solution is added dropwise to a refluxing solution of 8 g (0.051 moles) of phenyl chloroformate in 10 ml of toluene. The reaction mixture is refluxed for 24 hours. Thereafter the solvent is evaporated under a pressure of 100 mmHg and the excess of phenyl chloroformate is removed under a pressure of 5 mmHg. The evaporation residue is admixed with 10 ml of ethanol and the mixture is evaporated in vacuo. 8-Ethoxycarbonyl-3-phenoxycarbonyloxy-nortropane is obtained as a light yellow oily residue. This substance is admixed with 10 ml of ethanol and 2 g (0.04 moles) of hydrazine hydrate, the mixture is allowed to stand at room temperature for 2 days, and then the solution is evaporated in vacuo. The oily residue is taken up in 20 ml of chloroform and the solution is washed with 4×10 ml of distilled water until neutral. The chloroform solution is dried over magnesium sulfate, filtered, and the filtrate is evaporated. The residue is dissolved in 10 ml of ethanol, 4 ml of a 22% ethanolic hydrochloric acid solution are added, and the solution is admixed with diethyl ether (the addition of diethyl ether is stopped just before the solution becomes hazy). The mixture is allowed to stand in a refrigerator overnight, thereafter the separated crystals are filtered off, washed with ether and dried.

After recrystallization from ethanol in the presence of diethyl ether 3.2 g (40 %) of 8-ethoxycarbonyl-3α-hydrazinocarbonyloxy-nortropane hydrochloride are obtained; m.p.:185°-187° C.

Analysis: Calculated for $C_{11}H_{20}N_3O_4Cl$: C: 45.00%, H: 6.81%, N: 14.31%, Cl: 12.10%, Found: C: 44.64%, H: 7.01%, N: 14.30%, Cl: 12.32%,

EXAMPLE 2

8-Ethoxycarbonyl-3α-hydrazinocarbonyloxy-nortropane hydrochloride 30 g of phosgene are absorbed in 100 ml of absolute benzene. The solution is cooled to −5° C, and a mixture of 10.70 g (0.058 moles) of 8-ethoxycarbonyl-nortropine, 7.9 g (0.10 moles) of absolute pyridine and 100 ml of absolute benzene is added dropwise to the solution within 1 hour. During addition the temperature of the mixture is maintained below 0° C. The reaction mixture is stirred for additional 1 hour at 20° C, then it is poured onto 200 g of icy water, and the mixture is shaken in a separatory funnel for 30 minutes. The phases are separated and the above operation is repeated once more. The benzene phase is dried over magnesium sulfate, filtered, and the filtrate is evaporated at room temperature in vacuo to a final volume of about 40 ml. This concentrate is added slowly to a stirred mixture of 10 g (0.20 moles) of hydrazine hydrate, 50 ml of benzene and 30 ml of ethanol; addition is performed at a temperature below 10° C. The mixture is allowed to stand at room temperature overnight and then it is evaporated in vacuo. The residue is taken up in 50 ml of chloroform, the solution is washed several times with water, and the resulting neutral solution is dried and evaporated. The oily residue is taken up in 20 ml of ethanol, 10 ml of a 22% ethanolic hydrochloric acid solution are added, and the solution is admixed with diethyl ether (the addition of diethyl ether is stopped just before the solution becomes hazy). The mixture is allowed to stand in a refrigerator overnight, then the separated snow-white crystals are filtered off and recrystallized as described in Example 1. 9.8 g (57%) of 8-ethoxycarbonyl-3α-hydrazinocarbonyloxynortropane hydrochloride are obtained; m.p.: 185-187° C. The product is identical with the product of Example 1 (the mixture of the two products melts at 185°-187° C).

EXAMPLE 3

8-Phenoxycarbonyl-3α-hydrazinocarbonyloxy-nortropane

A solution of 90 g (0.64 moles) of dry tropine in 100 ml of absolute benzene is added dropwise and slowly to a stirred refluxing mixture of 300 g (1.91 moles) of phenyl chloroformate and 200 ml of absolute benzene. The reaction mixture is stirred and refluxed for 24 hours. A bubbling flask, filled with benzene, is attached to the top of the reflux condenser. At the beginning of the reaction vigorous bubbling is observed, which indicates the formation and escape of methyl chloride and hydrochloric acid. At the beginning of the reaction a small amount of crystalline substance separates, which dissolves later on. After 24 hours of refluxing the light brown solution is evaporated to remove benzene and the excess of phenyl chloroformate. The brown oily residue is admixed with 200 ml of ethanol and the mixture is allowed to stand in a refrigerator overnight. The separated crystals are filtered off, washed with ethanol, and the resulting white crystalline substance is dried under an I.R. lamp. 177..0 g (76%) of crude 8-phenoxycarbonyl-3α-phenoxycarbonyloxy-nortropane are obtained; m.p.: 102°-104° C. After recrystallization from ethanol 155.7 g (67%) of a pure substance is obtained; m.p.: 107°-108° C.

Analysis: Calculated for $C_{14}H_{17}N_3O_3$: C: 68.65%, H: 5.75%, N: 3.82%. Found: C: 68.62%, H: 6.45%, N: 4.01%.

30 g (0.082 moles) of 8-phenoxycarbonyl-3α-phenoxy-carbonyloxy-nortropane and 6 g (0.12 moles) of hydrazine hydrate are dissolved in 100 ml of absolute ethanol at 50° to 60° C, and the resulting solution is allowed to stand at room temperature overnight. The separate crystalline substance is filtered off, washed with ethanol and dried. 22.90 g (91.5%) of 8-phenoxycarbonyl-3α-hydrazinocarbonyloxy-nortropane are obtained; m.p.: 175°-178° C. After recrystallization from tenfold amount of ethanol 21.50 g (86.00%) of pure product are obtained; m.p.: 183°-184° C. Analysis: Calculated for $C_{15}H_{19}N_3O_4$: C: 59.10%, H: 6.35%, N: 13.79%. Found: C: 59.36%, H: 6.35%, N: 13.76%.

EXAMPLE 4

8-Phenoxycarbonyl-3α-hydrazinocarbonyloxy-nortropane 70.60 g (0.50 moles) of dry tropine are dissolved in 100 ml of benzene, and the solution is added dropwise at 20° C to a stirred mixture of 156.5 g (1.00 mole) of phenyl chloroformate and 200 ml of absolute benzene. The reaction mixture is stirred for 3 hours at 20° C. The separated crystalline product is filtered off, washed with benzene and water, dried and recrystallized from benzene. 54.6 g (44.5%) of 8-phenoxycarbonyl-nortropine are obtained; m.p.: 151°-153° C.

12.0 g (0.48 moles) of 8-phenoxycarbonyl-nortropine are dissolved in 100 ml of chloroform, and the solution is added dropwise to a stirred solution of 30 g of phosgene in 150 ml of chloroform. During addition the temperature of the mixture is maintained below 0° C. Thereafter one proceeds as described in Example 2. 13.5 g (92%) of 8-phenoxycarbonyl-3δ-hydrazinocarbonyloxy-nortropane are obtained.

EXAMPLE 5

8-Phenoxycarbonyl-3α-hydrazinocarbonyloxy-nortropane hydrochloride 43.0 g (0.14 moles) of 8-phenoxycarbonyl-3α-hydrazinocarbonyloxy-nortropane are dissolved in 50 ml of 22% ethanolic hydrochloric acid under gentle heating (40 to 50° C). The solution is decolourized with charcoal, filtered, cooled to 20° C and admixed with diethyl ether (the addition of diethyl ether is stopped just before the mixture becomes hazy; this requires about 150 ml of diethyl ether). The mixture is cooled with ice water, and the separated crystals are filtered off and dried. 38.00 g (79%) of 8-phenoxycarbonyl-3α-hydrazinocarbonyloxy-nortropane hydrochloride are obtained; m.p.: 217°-219° C. When evaporating the mother liquor and treating the residue with ether further 6.00 g (12.5%) of the product are isolated; m.p.: 217°-219° C.

Analysis: Calculated for $C_{15}H_{20}N_3ClO_4$: C: 53.00%, H: 5.89%, N: 12.31%, Cl: 10.40%. Found: C: 52.74%, H: 6.20%, N: 12.24%, Cl: 9.94%.

EXAMPLE 6

8-Phenoxycarbonyl-3α-hydrazinocarbonyloxy-nortropane hydrobromide 6.1 g (0.02 moles) of 8-phenoxycarbonyl-3α-hydrazinocarbonyloxy-nortropane are dissolved in a mixture of 10 ml of ethanol and 2.2 g of 48% aqueous hydrogen bromide. The solution is decolourized with activated carbon, filtered, and ether is added to the filtrate until it becomes hazy. The mixture is cooled with ice water, the separated crystals are filtered off, and washed with diethyl ether. The mother liquor is processed as described in Example 5. A total amount of 7.40 g (96%) of 8-phenoxycarbonyl-3α-hydrazinocarbonyl-oxy-nortropane hydrobromide is obtained; m.p.: 202°-216° C.

Analysis: Calculated for $C_{15}H_{20}N_3BrO_4$: C: 46.60%, H: 5.18%, N: 10.88%, Br: 20.62%. Found: C: 46.53%, H: 5.41%, N: 10.85% Br: 20.84%.

EXAMPLE 7

8-Phenoxycarbonyl-3α-hydrazinocarbonyloxy-nortropane sulfate 6.10 g (0.02 moles) of 8-phenoxycarbonyl-3α-hydrazinocarbonyloxy-nortropane are dissolved in a mixture of 10 of ethanol and 2.2 g of concentrated sulfuric acid. The solution is decolourized with activated carbon, filtered, and the filtrate is admixed with ether. The separated crystals are filtered off, washed with ether and dried. 7.9 g (98%) of 8-phenoxycarbonyl-3α-hydrazinocarbonyloxy-nortropane sulfate are obtained; m.p.: 168°-171.5° C.

Analysis: Calculated for $C_{15}H_{21}N_3O_8S$: C: 44.80% H: 5.24% N: 10.45% S: 7.94%. Found: C: 44.44% H: 5.51% N: 10.08% S: 7.85%.

EXAMPLE 8

8-Phenoxycarbonyl-3α-hydrazinocarbonyloxy-nortropane phosphate 3.50 g (0.011 moles) of 8-phenoxycarbonyl-3α-hydrazinocarbonyloxy-nortropane are dissolved in a mixture of 10 ml of methanol and 2.5 g of 80% phosphoric acid. Thereafter one proceeds as describd in Example 7. 4.5 g (97%) of 8phenoxycarbonyl-3α-hydrazinocarbonyloxy-nortropane phosphate are obtained; m.p.: 194.2°–198.5° C.
Analysis: Calculated for $C_{15}H_{22}N_3O_8P$: C: 44.75% H: 5.50% N: 10.45% P: 7.67%. Found: C: 44.67% H: 5.54% N: 10.30% P: 7.29%.

EXAMPLE 9

8-Phenoxycarbonyl-3α-hydrazinocarbonyloxy-nortropane p-toluenesulfonate 6.1 g (0.02 moles) of 8-phenoxycarbonyl-3α-hydrazino-carbonyloxy-nortropane are dissolved in a mixture of 20 ml of methanol and 5.0 g of P-toluenesulfonic acid monohydrate. Thereafter one proceeds as described in Example 7. 8.00 g (84%) of 8-phenoxycarbonyl-3αhydrazinocarbonyloxy-nortropane p-toulenesulfonate are obtained; m.p.: 109.8°–114.5° C.
Analysis: Calculated for $C_{22}H_{27}N_3O_7S$: C: 55.48%, H: 5.70%, N: 8.78%, S: 6.70%. Found: C: 53.66%, H: 6.08%, N: 8.40%, S: 6.50%.

EXAMPLE 10

8-Phenoxycarbonyl-3α-hydrazinocarbonyloxy-nortropane

A solution of 14.1 g (0.1 moles) of dry tropine in 30 ml of chloroform is added dropwise within 30 minutes to a stirred refluxing solution of 19.0 g (0.122 moles) of phenyl chloroformate in 20 ml of chloroform. The reaction mixture is refluxed with stirring for 3 hours. A clear solution is obtained, which is not alkaline. The solution is evaporated in vacuo, the residue is admixed with a small amount of methanol, and evaporated again. The resulting yellowish-white crystalline substance is filtered off and washed with 9 1:2 mixture of benzene and petroleum ether. 20.6 g (83.5%) of crystalline 8-phenoxycarbonyl-nortropine are obtained; m.p.: 149°–150° C.

This product is dissolved in threefold amount of ethanol, the solution is decolourized with activated carbon, filtered, and warm water (about 50° C) is added to the still warm solution until it becomes hazy. The product is crystallized. 18.0 g (73%) of purified 8-phenoxycarbonyl-nortropine are obtained; m.p.: 151°–153° C.

Thereafter one proceeds as described in Example 4 to obtain 8-phenoxycarbonyl-3α-hydrazinocarbonyloxy-nortropane melting at 183°–184° C.

EXAMPLE 11

8-Phenoxycarbonyl-3α-(2′-methyl-hydrazinocarbonyloxy)-nortropane 9.2 g (0.2 moles) if methylhydrazine are added to a solution of 18.3 g (0.05 moles) of 8-phenoxycarbonyl-3α-phenoxycarbonyloxy-nortropane in 30 ml of chlorobenzene, and the mixture is boiled at 120° C for 7 hours. The mixture is cooled to 20° C, poured into a separatory funnel and washed repeatedly with water until neutral. A mixture of 6 ml of concentrated hydrochloric acid and 30 ml of ice water is added to the chlorobenzene phase, and the resulting emulsion is maintained at 0° C for 2 hours with occasional shaking. The separated crystalline product is filtered off, washed with ice water until neutral and dried at room temperature. 12.10 g of 8-phenoxycarbonyl-3α-(2′-methyl-hydrazinocarbonyloxy)-nortropane are obtained as snow-white crystals.

The obtained product is dissolved in 40 ml of warm benzene, the solution is decolourized, filtered, and petrol is added to the filtrate cautiously until it becomes hazy. The mixture is cooled, the separated crystals are filtered off and washed with petrol. 7.6 g (47.8%) of purified substance are obtained; m.p.: 95°–98° C.
Analysis: Calculated for $C_{16}H_{21}N_3O_4$: C: 60.17%, H: 6.63%, N: 13.16%. Found: C: 59.60%, H: 6.96%, N: 13.63%.

EXAMPLE 12

8-Phenoxycarbonyl-3α-(2′-/2″-hydroxyethyl/-hydrazinocarbonyloxy)-nortropane 29.4 g (0.08 moles) of 8-phenoxycarbonyl-3α-phenoxycarbonyloxy-nortropane are dissolved in 70 ml of chlorobenzene with heating, and 7.6 g (0.15 moles) of hydroxyethylhydrazine are added to the solution. The reaction mixture is stirred at 120° C for 7 hours. The mixture is cooled, washed with water until neutral, dried over magnesium sulfate, and evaporated under reduced pressure (10 mmHg). The oily residue is taken up in a mixture of 10 ml of concentrated hydrochloric acid and 70 ml of ice water. The resulting clear solution is extracted thrice with ether. and the aqueous phase is stored in a refrigerator. The separated crystalline product is filtered off, washed with water and dried under an I.R. lamp. The resulting 15.30 g of white, crystalline substance are dissolved in 25 ml of ehtanol, the solution is decolourized, filtered, and the filtrate is admixed with 10 ml of 1 n aqueous hydrochlorice acid. The mixture is stored in a refrigerator. The separated crystals are filtered off, washed with alcohol and dried under an I.R. lamp. 8.5 g (30.4%) of purified 8-phenoxycarbonyl-3α-(2′-/2″-hydroxy-ethyl/-hydrazinocarbonyloxy)-nortropane are obtained as a white, crystalline substance; m.p.: 183°–196° C.
Analysis: Calculated for $C_{17}H_{23}N_3O_5$: C: 58.44%, H: 6.63%,N: 12.03%.
Found: C: 58.40%, H:6.56%, N: 12.00%.

EXAMPLE 13

8-Phenoxycarbonyl-3α-ethylidene-hydrazinocarbonyloxy-nortropane 2.5 g (0.056 moles) of acetyldehyde are added to a solution of 11.7 g (0.038 moles) of 8-phenoxycarbonyl-3α-hydrazinocarbonyloxy-nortropane in 25 ml of methanol, and the mixture is shaken at 20° C for 5 minutes. The resulting clear solution is allowed to stand at 0° C overnight.

The separated crystals are filtered off, washed with a small amount of a 1:1 mixture of methanol and water, an dried. 12.20 g (96.13%) of 8-phenoxycarbonyl-3α-(ethyl-idene-hydrazinocarbonyloxy)-northropane are obtained; m.p.: 146°–148° C.

The product is dissolved in 50 ml of hot methanol, and the solution is decolourzed and filtered. 10 ml of water are added to the still warm filtrate and it is cooled slowly. The mixture is stored for 3 hours in a refrigerator, and the separated crystals are filtered off and dried. 11.10 g (87.41%) of a purified product are obtained; m.p.: 146°–148° C.

Analysis: Calculated for $C_{17}H_{21}N_3O_4$: C: 61.62%, H: 6.39%, N: 12.68%. Found C: 62.47%, H: 6.43%, N: 12.98%.

EXAMPLE 14

8-Phenoxycarbonyl-3α-(2',2'-diacetyl-hydrazinocarbonyloxy)-nortropane 15.26 g (0.05 moles) of 8-phenoxycarbonyl-3α-hydroazinocarbonyloxy-nortropane are added to 20 ml of acetyl-chloride, and the mixture is stirred slowly. The solid dissolves and the mixture warms to 40° C. The mixture is allowed to stand at 20° C for one day, and the excess of acetyl-chloride is evaporated. The residue is triturated with petrol and the separated crystals are filtered off. 14 g of 8-phenocarbonyl-3α-(2',2'-diacetyl-hydrazinocarbonyloxy)-nortropane are obtained; m.p.: 172°–174° C.

The product is dissolved in hot ethanol, the solution is decolourized, filtered, and admixed with petrol. 12 g (61.6 %) of a purified crystalline product are obtained. Analysis: Calculated for $C_{19}H_{23}N_3O_6$: C: 58.60%, H: 5.95%, N: 10.79%. Found: C: 58.50%, H: 6.03%, N: 10.76%.

EXAMPLE 15

8-Phenoxycarbonyl-3β-hydrozinocarbonyloxy-nortropane (A) A solution of 14.1 g (0.1 moles) of tropane-3β-ol (pseudotropine) in 60 ml of absolute benzene is added dropwise to a stirred mixture of 31.3 g (0.2 moles) of phenyl chloroformate and 100 ml of absolute benzene. During addition the mixture is cooled with water. Thereafter the mixture is stirred for 6 hours. The separated crystalline substance is filtered off, washed with benzene and dried. 19.00 g (63.8%) of 3β-phenoxycarbonyloxy-tropane hydrochloride are obtained.

(B) The crystalline substance is dissolved in 50 ml of water and the small amount of insoluble substance is filtered off. The base is liberated from its salt by adding a calculated amount (5.22 g) of sodium hydrocarbonate to the solution. The solution is extracted thrice with chloroform. The chloroform solutions are combined, dried over magnesium sulfate, filtered, and the filtrate is evaporated. 14.72 g (91%) of 3β-phenoxycarbonyloxy-tropane are obtained as a viscous oil.

(C) The obtained tropane base is admixed with 25 ml of benzene, and this solution is added dropwise to a stirred refluxing mixture of 13 ml of phenyl chloroformate and 25 ml of benzene. After addition the reaction mixture is refluxed with stirring until the cessation of gas development (1 hour). The reaction mixture is cooled to 20° C, the separated small amount of crystalline quaternary salt is filtered off, and the filtrate is evaporated in vacuo. 30 ml of ethanol are added to the 22.4 g of yellowish oily residue and the oil is triturated. A crystalline substance is formed. The mixture is stored in a refrigerator (0° C) for 3 hours, thereafter the crystals are filtered off, washed with 2×8 ml of ethanol and dried. 14.80 g (71.7%) of 8-phenoxycarbonyl-3β-phenoxycarbonyloxy-nortropane are obtained; m.p.: 126°–128° C.

(D) A mixture of 12.24 g (0.033 moles) of 8-phenoxycarbonyl-3β-phenoxycarbonyloxy-nortropane, 100 ml of ethanol and 2.0 g (0.04 moles) of hydrazine hydrate is heated to boiling, whereupon the solids dissolve. The resulting solution is refluxed for 4 hours and then it is allowed to stand at 20° C overnight. The solution is evaporated, the residue is taken up in 50 ml of chloroform, and the chloroform solution is washed several times with water until the wash becomes neutral. The chloroform solution is evaporated, the residue is taken up in 50 ml of petrol, and the mixture is stored for 2 days in a refrigerator. The separated crystals are filtered off, dissolved in 20 ml of hot benzene, the solution is decolourized, filtered, and the filtrate is admixed with petroleum ether. The mixture is cooled and the crystalline substance is separated. 9 g (86%) of 8-phenoxycarbonyl-3β-hydrazinocarbonyloxy-nortropane are obtained; m.p.: 88°–90° C.

Analysis: Calculated for $C_{15}H_{19}N_3O_4$:
C: 59.10%, H: 6.26%, N: 13.79%. Found: C: 59.45%, H: 6.50%, N: 13.68%.

What we claim is:

1. A nortropinone-carbazate derivative of the formula (I),

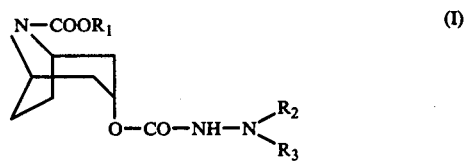

wherein
$R_1$ is a $C_{1-4}$ alkyl, phenyl or halophenyl group,
$R_2$ is hydrogen or a $C_{1-4}$ alkyl, hydroxy-$C_{1-4}$alkyl, $C_{1-4}$acyl, phenoxycarbonyl or $C_{1-4}$alkoxycarbonyl group, and
$R_3$ is hydrogen or a $C_{1-4}$ alkyl or $C_{1-4}$ acyl group, or
$R_2$ and $R_3$ may form together a $C_{1-10}$ alkylene group attached to the nitrogen atom with a double bond, or a pharmaceutically acceptable acid addition salt thereof.

2. 8-Ethoxycarbonyl-3α-hydrazinocarbonyloxy-nortropane hydrochloride.
3. 8-Phenoxycarbonyl-3α-hydrazinocarbonyloxy-nortropane.
4. 8-Phenoxycarbonyl-3α-hydrazinocarbonyloxy-nortropane hydrochloride.
5. 8-Phenoxycarbonyl-3α-hydrazinocarbonyloxy-nortropane hydrobromide.
6. 8-Phenoxycarbonyl-3α-hydrazinocarbonyloxy-nortropane sulfate.
7. 8-Phenoxycarbonyl-3α-hydrazinocarbonyloxy-nortropane phosphate.
8. 8-Phenoxycarbonyl-3α-hydrazinocarbonyloxy-nortropane p-toluenesulfonate.
9. 8-Phenoxycarbonyl-3α-(2'-methyl-hydrazinocarbonyl-oxy)-nortropane.
10. 8-Phenoxycarbonyl-3α-(2'-/2''-hydroxyethyl/-hydrazinocarbonyloxy-nortropane.
11. 8-Phenoxycarbonyl-3α-(ethylidene-hydrazinocarbonyl-oxy)-nortropane.
12. 8-Phenoxycarbonyl-3α-(2',2'-diacetyl-hydrazinocarbonyloxy)-nortropane.
13. 8-Phenoxycarbonyl-3β-hydrazinocarbonyloxy-nortropane.
14. A narcosis potentiating pharmaceutical composition containing an effective amount of a compound as defined in claim 1, and a conventional pharmaceutical adjuvant and/or auxiliary agent.

* * * * *